United States Patent [19]

Dellaria et al.

[11] Patent Number: 5,346,914

[45] Date of Patent: Sep. 13, 1994

[54] (4-ALKOXYPYRAN-4-YL) SUBSTITUTED ARYLALKYLARYL-, ARYLALKENYLARYL-, AND ARYLALKYNYLARYLUREA INHIBITORS OF 5-LIPOXYGENASE

[75] Inventors: Joseph F. Dellaria, Lindenhurst; Anwer Basha, Lake Forest; Lawrence A. Black, Vernon Hills; Linda J. Dorn, Arlington Heights; Wendy Lee, Chicago, all of Ill.

[73] Assignee: Abbott Laboratories, Abbott Park, Ill.

[21] Appl. No.: 61,988

[22] Filed: May 14, 1993

[51] Int. Cl.$^5$ ............... A61K 31/35; A61K 31/415; A61K 31/495; C07D 309/10; C07D 405/10; C07D 405/12
[52] U.S. Cl. ............... 514/402; 514/311; 514/314; 514/460; 514/227.5; 514/231.5; 514/255; 514/274; 548/311.1; 548/315.7; 549/419; 544/58.4; 544/176; 544/315; 544/316; 544/318; 544/388
[58] Field of Search ............... 514/460, 311, 314, 402, 514/227.6, 231.5, 255, 274; 548/311.1, 315.7; 549/419; 544/58.4, 176, 315, 316, 368, 388

[56] References Cited

U.S. PATENT DOCUMENTS

| | | | |
|---|---|---|---|
| 3,671,539 | 6/1972 | Saucy | 549/419 X |
| 4,897,382 | 1/1990 | della Valle et al. | 514/25 |
| 5,155,229 | 10/1992 | DiPietro et al. | 548/336.1 |
| 5,208,259 | 5/1993 | Bird et al. | 514/460 |
| 5,276,037 | 1/1994 | Dowell et al. | 514/253 |

FOREIGN PATENT DOCUMENTS

| | | | |
|---|---|---|---|
| 53-105478 | 9/1978 | Japan | 549/419 |
| 0401664 | 10/1973 | U.S.S.R. | 549/419 |

*Primary Examiner*—Floyd D. Higel
*Attorney, Agent, or Firm*—Jerry F. Janssen

[57] ABSTRACT

Compounds of the structure

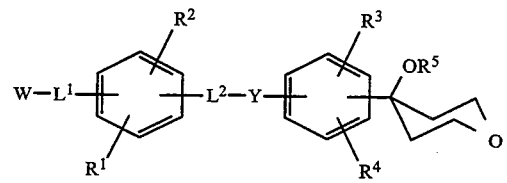

wherein W is selected from

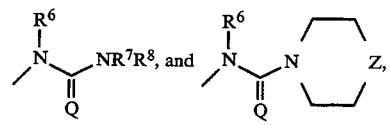

where Q is oxygen or sulfur, $R^6$ and $R^7$ are hydrogen or alkyl, or $R^6$ and $R^7$, together with the nitrogen atoms to which they are attached, define a radical of formula

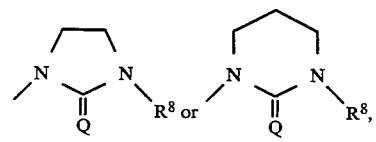

$R^8$ is selected from hydrogen, alkyl, haloalkyl, optionally substituted phenyl, hydroxyalkyl, aminoalkyl, carboxyalkyl, (alkoxycarbonyl)alkyl, and (alkylaminocarbonyl)alkyl; Z is —CH$_2$—, oxygen, sulfur, or —NR$^9$ where R$^9$ is hydrogen or alkyl, L$^1$ and L$^2$ are selected from a valence bond, alkylene, propenylene, and propynylene, R$^1$, R$^2$, R$^3$, and R$^4$ are independently selected from alkyl, haloalkyl, halogen, cyano, amino, alkoxycarbonyl, and dialkylaminocarbonyl, Y is selected from oxygen, —NR$^{10}$, where R$^{10}$ is hydrogen or alkyl, and $$\underset{-S-,}{(O)_n}$$

where n=0, 1, or 2, and R$^5$ is alkyl, inhibit the biosynthesis of leukotrienes. These compounds are useful in the treatment or amelioration of allergic and inflammatory disease states.

16 Claims, No Drawings

(4-ALKOXYPYRAN-4-YL) SUBSTITUTED ARYLALKYLARYL-, ARYLALKENYLARYL-, AND ARYLALKYNYLARYLUREA INHIBITORS OF 5-LIPOXYGENASE

TECHNICAL FIELD

This invention relates to compounds having biological activity to inhibit lipoxygenase enzymes, to pharmaceutical compositions comprising these compounds, and to a medical method of treatment. More particularly, this invention concerns certain (4-alkoxypyran-4-yl) substituted arylalkylaryl-, arylalkenylaryl-, and arylalkynylarylurea compounds which inhibit leukotriene biosynthesis, to pharmaceutical compositions comprising these compounds and to a method of inhibiting lipoxygenase activity and leukotriene biosynthesis.

BACKGROUND OF THE INVENTION

5-Lipoxygenase is the fast dedicated enzyme in the pathway leading to the biosynthesis of leukotrienes. This important enzyme has a rather restricted distribution, being found predominantly in leukocytes and mast cells of most mammals. Normally 5-lipoxygenase is present in the cell in an inactive form; however, when leukocytes respond to external stimuli, intracellular 5-lipoxygenase can be rapidly activated. This enzyme catalyzes the addition of molecular oxygen to fatty acids with cis,cis-1,4-pentadiene structures, convening them to 1-hydroperoxy-trans,cis,-2,4-pentadienes. Arachidonic acid, the 5-lipoxygenase substrate which leads to leukotriene products, is found in very low concentrations in mammalian cells and must fast be hydrolyzed from membrane phospholipids through the actions of phospholipases in response to extracellular stimuli. The initial product of 5-lipoxygenase action on arachidonate is 5-HPETE which can be reduced to 5-HETE or convened to $LTA_4$. This reactive leukotriene intermediate is enzymatically hydrated to $LTB_4$ or conjugated to the tripeptide glutathione to produce $LTC_4$. $LTA_4$ can also be hydrolyzed nonenzymatically to form two isomers of $LTB_4$. Successive proteolytic cleavage steps convert $LTC_4$ to $LTD_4$ and $LTE_4$. Other products resulting from further oxygenation steps have also been described in the literature. Products of the 5-lipoxygenase cascade are extremely potent substances which produce a wide variety of biological effects, often in the nanomolar to picomolar concentration range.

The remarkable potencies and diversity of actions of products of the 5-lipoxygenase pathway have led to the suggestion that they play important roles in a variety of diseases. Alterations in leukotriene metabolism have been demonstrated in a number of disease states including asthma, allergic rhinitis, rheumatoid arthritis and gout, psoriasis, adult respiratory distress syndrome, inflammatory bowel disease, endotoxin shock syndrome, atherosclerosis, ischemia induced myocardial injury, and central nervous system pathology resulting from the formation of leukotrienes following stroke or subarachnoid hemorrhage.

The enzyme 5-lipoxygenase catalyzes the first step leading to the biosynthesis of all the leukotrienes and therefore inhibition of this enzyme provides an approach to limit the effects of all the products of this pathway. Compounds which inhibit 5lipoxygenase are thus useful in the treatment of disease states such as those listed above in which the leukotrienes play an important role.

SUMMARY OF THE INVENTION

In its principal embodiment, the present invention provides certain triether compounds which inhibit lipoxygenase enzyme activity and are useful in the treatment of allergic and inflammatory disease states in which leukotrienes play a role.

The compounds of this invention and the pharmaceutically acceptable salts thereof have the structure

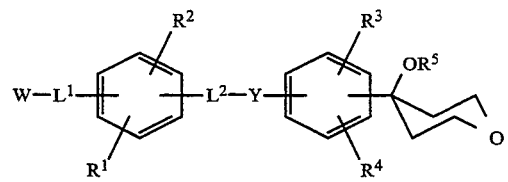

wherein W is selected from the group consisting of

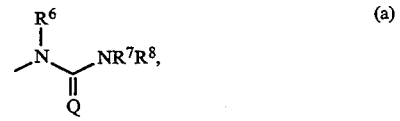 (a)

and

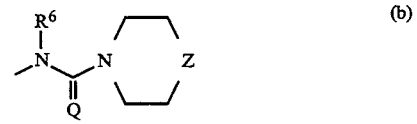 (b)

where Q is oxygen or sulfur, $R^6$ and $R^7$ are independently selected from the group consisting of hydrogen and alkyl of one to four carbon atoms, provided that when $L^1$ is a valence bond, $R^6$ is alkyl of one to four carbon atoms, or $R^6$ and $R^7$, together with the nitrogen atoms to which they are attached, define a radical of formula

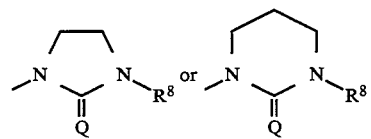

$R^8$ is selected from a) hydrogen; b) alkyl of one to four carbon atoms; c) haloalkyl of one to four carbon atoms; d) phenyl, optionally substituted with alkyl of one to four carbon atoms, alkoxy of one to four carbon atoms, haloalkyl, or halogen; e) hydroxyalkyl of one to four carbon atoms; f) aminoalkyl of one to four carbon atoms; g) carboxyalkyl of one to four carbon atoms; h) (alkoxycarbonyl)alkyl where the alkyl and alkoxy portions each are of one to four carbon atoms; and i) (alkylaminocarbonyl)alkyl, where the alkyl and aminoalkyl portions each are of one to four carbon atoms, and Z is $-CH_2-$, oxygen, sulfur, or $-NR^9$ where $R^9$ is hydrogen or alkyl of one to four carbon atoms.

$L^1$ is a valence bond or is selected from alkylene of one to three carbon atoms, propenylene, and propynylene. $R^1$, $R^2$, $R^3$, and $R^4$ are independently selected from alkyl of one to four carbon atoms, alkoxy of one to four carbon atoms, haloalkyl, halogen, cyano, amino, alkoxycarbonyl of one to four carbon atoms, and dialkylaminocarbonyl where the alkyl portions are each of one to four carbon atoms. $L^2$ is a valence bond or is selected from alkylene of one to three carbon atoms, propenylene, and propynylene, Y is selected from the group consisting of oxygen, $>NR^9$, where $R^9$ is hydrogen or alkyl of one to four carbon atoms, and $$-S-\overset{(O)_n}{\underset{}{}}-,$$

where n=0, 1, or 2, and $R^5$ is alkyl of one to four carbon atoms.

DETAILED DESCRIPTION OF THE INVENTION

Definitions of Terms

As used throughout this specification and the appended claims, the term "alkyl" refers to a monovalent group derived from a straight or branched chain saturated hydrocarbon by the removal of a single hydrogen atom. Alkyl groups are exemplified by methyl, ethyl, n- and iso-propyl, n-, sec-, iso- and tert-butyl, and the like.

The term "alkylamino" refers to a group having the structure —NHR' wherein R' is alkyl as previously defined. Example of alkylamino include methylamino, ethylamino, iso-propylamino, and the like.

The term "alkylaminocarbonyl" refers to an alkylamino group, as previously defined, attached to the parent molecular moiety through a carbonyl group. Examples of alkylaminocarbonyl include methylaminocarbonyl, ethylaminocarbonyl, iso-propylaminocarbonyl, and the like.

The term "alkanoyl" refers to an alkyl group, as defined above, attached to the parent molecular moiety through a carbonyl group. Alkanoyl groups are exemplified by formyl, acetyl, butanoyl, and the like.

The term "propynyl" refers to a straight chain, three-carbon group containing a carbon-carbon triple bond.

The term "hydroxyalkyl" represents an alkyl group, as defined above, substituted by one to three hydroxyl groups with the proviso that no more than one hydroxy group may be attached to a single carbon atom of the alkyl group.

The term "haloalkyl" denotes an alkyl group, as defined above, having one, two, or three halogen atoms attached thereto and is exemplified by such groups as chloromethyl, bromoethyl, trifluoromethyl, and the like.

The terms "alkoxy" and "alkoxyl" denote an alkyl group, as defined above, attached to the parent molecular moiety through an oxygen atom. Representative alkoxy groups include methoxyl, ethoxyl, propoxyl, butoxyl, and the like.

The term "alkoxycarbonyl" represents an ester group; i.e. an alkoxy group attached to the parent molecular moiety through a carbonyl group. Representative alkoxycarbonyl groups include methoxycarbonyl, ethoxycarbonyl, and the like.

The term "alkenyl" denotes a monovalent group derived from a hydrocarbon containing at least one carbon-carbon double bond by the removal of a single hydrogen atom. Alkenyl groups include, for example, ethenyl, propenyl, butenyl, 1-methyl-2-buten-1-yl and the like.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "aminoalkyl" denotes an —NH2 group attached to the parent molecular moiety through an alkylene group. Representative aminoalkyl groups include 2-amino-1-ethylene, 3-amino-1-propylene, 2-amino-1-propylene, and the like.

The term "carboxyalkyl" denotes a —CO2H group attached to the parent molecular moiety through an alkylene group. Representative carboxyalkyl groups include, 1-carboxyethyl, 2-carboxyethyl, 1-carboxypropyl, and the like.

The term "(alkoxycarbonyl)alkyl" denotes an alkoxycarbonyl group, as defined above, attached to the parent molecular moiety through an alkylene group. Representative (alkoxycarbonyl)alkyl groups include ethoxycarbonylmethyl, ethoxycarbonylethyl, methoxycarbonylpropyl, and the like.

The term "(alkylaminocarbonyl)alkyl" denotes an alkylaminocarbonyl group, as defined above, attached to the parent molecular moiety through an alkylene group. Examples of (alkylaminocarbonyl)alkyl groups include methylaminocarbonylmethyl, methylaminocarbonylpropyl, isopropylaminocarbonylmethyl, and the like.

The term "alkenylene" denotes a divalent group derived from a straight or branched chain hydrocarbon containing at least one carbon-carbon double bond. Examples of alkenylene include —CH=CH—, —CH2CH=CH—, —C(CH3)=CH—, —CH2CH=CHCH2—, and the like.

In one preferred embodiment, the compounds of this invention have the structure wherein $R^4$ is hydrogen or halogen, and W, Y, and $R^5$ are as defined above.

Examples of compounds of this embodiment include, but are not limited to:

4-{3-[4-((N',N'-dimethylaminocarbonyl)aminomethyl)benzyloxy]-5-fluorophenyl}-4-methoxytetrahydropyran, 4-{3-[4-((N',N'-dimethylaminocarbonyl)aminomethyl)benzyloxy]phenyl}-4-methoxytetrahydropyran, 4-{3-[4-((N',N'-dimethylaminocarbonyl)aminomethyl)benzylthio]-5-fluorophenyl}-4-methoxytetrahydropyran, 4-{3-[4-((N',N'-dimethylaminocarbonyl)aminomethyl)benzylthio]phenyl}-4methoxytetrahydropyran, 4-{3-[4-((N',N'-dimethylaminocarbonyl)aminomethylbenzyl)amino]phenyl}4-methoxytetrahydropyran, 4-{3-[4-(((N',N'-dimethylaminocarbonyl)-N-methylamino)methyl)benzyloxy]-5-fluorophenyl}-4-methoxytetrahydropyran, 4-{3-[4-(2-imidazolidinon-1-ylmethyl)benzyloxy]-5-fluorophenyl}-4-methoxytetrahydropyran, 4-{3-[4-(imidazolidin-2-on-1-ylmethyl)benzyloxy]-phenyl}-4-methoxytetrahydropyran, 4-{3-[4-(imidazolidin-2-on-1-ylmethyl)benzylthio]-5-fluorophenyl}-4-methoxytetrahydropyran, and 4-{3-[4-(imidazolidin-2-on-1-ylmethyl)benzylthio]-5-fluorophenyl}-4-methoxytetrahydropyran.

In another preferred embodiment, the compounds of this invention have the structure

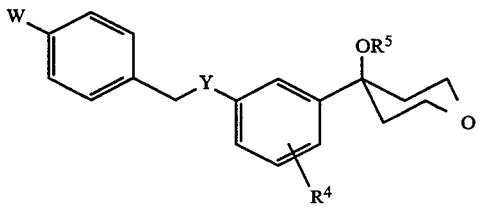

wherein $R^4$ is hydrogen or halogen, and W, Y, and $R^5$ are as defined above.

Examples of compounds of this embodiment include, but are not limited to:

4-{3-[4-((N',N'-dimethylaminocarbonyl)-N-methylamino)benzyloxy-5-fluorophenyl}-4-methoxytetrahydropyran, 4-{3-[4-((N',N'-dimethylaminothiocarbonyl)-N-methylamino)benzyloxy]-5-fluorophenyl}-4-methoxytetrahydropyran, 4-{3-[4-((N',N'-dimethylaminocarbonyl)-N-methylamino)benzyloxy]phenyl}-4-methoxytetrahydropyran, 4-{3-[4-((N',N'-dimethylaminocarbonyl)-N-methylaminobenzyl)amino]phenyl}-4-methoxytetrahydropyran, 4-{3-[4-((N',N'-dimethylaminothiocarbonyl)-N-methylaminobenzyl)amino]phenyl}-4-methoxytetrahydropyran, 4-{3-[4-((N',N'-dimethylaminocarbonyl)-N-methylamino)benzylthio]phenyl]-4-methoxytetrahydropyran, 4-{3-[4-((N',N'-dimethylaminocarbonyl)-N-methylamino)benzylthio]-5-fluorophenyl}-4-methoxytetrahydropyran, 4-{3-[4-((aminocarbonyl)amino)benzyloxy]-5-fluorophenyl}-4-methoxytetrahydropyran, 4-{3-[4-((aminocarbonyl)-N-methylamino)benzyloxy]-5-fluorophenyl}-4-methoxytetrahydropyran, 4-{3-[4-((N'-methylaminocarbonyl)-N-methylamino)benzyloxy]-5-fluorophenyl}-4-methoxytetrahydropyran, 4-{3-[4-((N'-methylaminocarbonyl)-amino)benzyloxy]-5-fluorophenyl}-4-methoxytetrahydropyran, 4-{3-[4-((1-piperidinylcarbonyl)-N-methylamino)benzyloxy]-5-fluorophenyl}-4-methoxytetrahydropyran, 4-{3-[4-((1-piperidinylcarbonyl)amino)benzyloxy]-5-fluorophenyl}-4-methoxytetrahydropyran, 4-{3-[4-((4-morpholinocarbonyl)-N-methylamino)benzyloxy]-5-fluorophenyl}-4-methoxytetrahydropyran, 4-{3-[4-((4-morpholinocarbonyl)amino)benzyloxy]-5-fluorophenyl}-4-methoxytetrahydropyran, 4-{3-[4-((4-thiomorpholinocarbonyl)-N-methylamino)benzyloxy]-5-fluorophenyl}-4-methoxytetrahydropyran, 4-{3-[4-((4-thiomorpholinocarbonyl)amino)benzyloxy]-5-fluorophenyl}-4-methoxytetrahydropyran, 4-{3-[4-((1-piperazinylcarbonyl)-N-methylamino)benzyloxy]-5-fluorophenyl}-4-methoxytetrahydropyran, 4-{3-[4-((1-piperazinylcarbonyl)amino)benzyloxy]-5-fluorophenyl}-4-methoxytetrahydropyran, 4-{3-[4-((1-piperazinylcarbonyl)-N-methylamino)benzyloxy]-5-fluorophenyl}-4-methoxytetrahydropyran, 4-{3-[4-(((N'-(3-bromoprop-1-yl)aminocarbonyl)-N-methylamino)benzyloxy]-5-fluorophenyl}-4-methoxytetrahydropyran, 4-{3-[4-(((N'-(3-aminoprop-1-yl)aminocarbonyl)-N-methylamino)benzyloxy]-5-fluorophenyl}-4-methoxytetrahydropyran, 4-{3-[4-(((N'-(3-hydroxyprop-1-yl)aminocarbonyl)-N-methylamino)benzyloxy]-5-fluorophenyl}-4-methoxytetrahydropyran, 4-{3-[4-(((N'-(3-ethoxycarbonylprop-1-yl)aminocarbonyl)-N-methylamino)benzyloxy]-5-fluorophenyl}-4-methoxytetrahydropyran, and 4- [3-[4-(((N'-(3-carboxyprop-1-yl)aminocarbonyl)-N-methylamino)benzyloxy[-5-fluorophenyl}-4-methoxytetrahydropyran.

In another preferred embodiment, the compounds of this invention have the structure

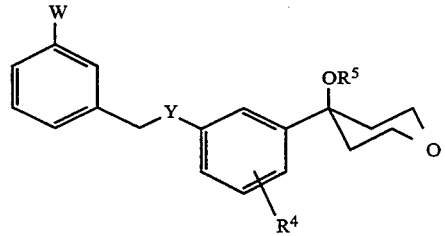

wherein W, Y, $R^4$, and $R^5$ are as defined above.

Examples of compounds of this embodiment include, but are not limited to:

4-{3-[3-((N',N'-dimethylaminocarbonyl)-N-methylamino)benzyloxy]-5-fluorophenyl}-4-methoxytetrahydropyran, 4-{3-[3-((N',N'-dimethylaminocarbonyl)-N-methylamino)benzyloxy]phenyl]-4-methoxytetrahydropyran, 4-{3-[3-((N',N'-dimethylaminocarbonyl)-N-methylaminobenzyl)amino]phenyl}-4-methoxytetrahydropyran, 4-{3-[3-((N',N'-dimethylaminocarbonyl)-N-methylamino)benzylthio]phenyl}-4-methoxytetrahydropyran, and 4-{3-[4-((N',N'-dimethylaminocarbonyl)-N-methylamino)benzylthio]-5-fluorophenyl}-4-methoxytetrahydropyran.

In a particularly preferred embodiment, the compounds of this invention have the structure

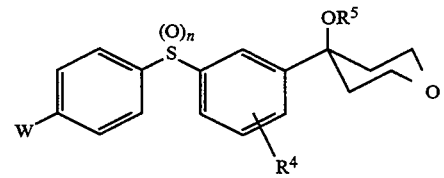

wherein n=0, 1, or 2, $R^4$ is hydrogen or halogen, and W and $R^5$ are as defined above.

Examples of compounds of this embodiment include, but are not limited to:

4-{3-[4-((N',N'-dimethylaminocarbonyl)-N-methylamino)phenylthio]phenyl}-4-methoxytetrahydropyran, 4-{3-[4-((N',N'-dimethylaminocarbonyl)-N-methylamino)phenylsulfinyl]phenyl}-4-methoxytetrahydropyran, and 4-{3-[4-((N',N'-dimethylaminocarbonyl)-N-methylamino)phenylsulfonyl]phenyl}-4-methoxytetrahydropyran.

Lipoxygenase Inhibition Determination

Inhibition of leukotriene biosynthesis was evaluated in an assay, involving calcium ionophore-induced $LTB_4$ biosynthesis expressed human whole blood. Human heparinized whole blood was preincubated with test compounds or vehicle for 15 min at 37° C. followed by calcium ionophore A23187 challenge (final concentration of 8.3 $\mu M$) and the reaction terminated after 30 min by adding two volumes of methanol containing prostaglandin $B_2$ as an internal recovery standard. The methanol extract was analyzed for $LTB_4$ using a commercially available radioimmunoassay.

The compounds of this invention inhibit leukotriene biosynthesis as illustrated in Table 1.

TABLE 1

| In Vitro Inhibitory Potencies of Compounds of this Invention Against 5-Lipoxygenase from Stimulated $LTB_4$ Formation in Human Whole Blood | |
|---|---|
| Example | $IC_{50}$ ($10^{-6}$ M) |
| 1 | 0.017 |
| 8 | 45% @ 0.025 $\mu M$ |
| 11 | 1.8 |
| 17 | 13% @ 200 nm |

Pharmaceutical Compositions

The present invention also provides pharmaceutical compositions which comprise compounds of the present invention formulated together with one or more non-toxic pharmaceutically acceptable carriers. The pharmaceutical compositions may be specially formulated for oral administration in solid or liquid form, for parenteral injection, or for rectal administration.

The pharmaceutical compositions of this invention can be administered to humans and other animals orally, rectally, parenterally, intracisternally, intravaginally, intraperitoneally, topically (as by powders, ointments, or drops), bucally, or as an oral or nasal spray. The term "parenteral" administration as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain pan of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carders such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound is mixed under sterile conditions with a pharmaceutically acceptable carrier and any needed preservatives, buffers, or propellants which may be required. Opthalmic formulations, eye ointments, powders and solutions are also contemplated as being within the scope of this invention.

Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon the activity of the particular compound, the route of administration, the severity of the condition being treated, and the condition and prior medical history of the patient being treated. However, it is within the skill of the art to start doses of the compound at levels lower than required for to achieve the desired therapeutic effect and to gradually increase the dosage until the desired effect is achieved.

Generally dosage levels of about 1 to about 50, more preferably of about 5 to about 20 mg of active compound per kilogram of body weight per day are administered orally to a mammalian patient. If desired, the effective daily dose may be divided into multiple doses for purposes of administration, e.g. two to four separate doses per day.

Preparation of the Compounds of this Invention

The compounds of this invention can be prepared by a variety of synthetic routes. Representative procedures are outlined as follows. It should be understood that $R^5$, $R^6$, $R^7$, $R^8$, and W as used herein correspond to the groups identified above.

A general route to the compounds of this invention is shown in Scheme 1. Reaction of 2, prepared as described in EPA 375 404, with sodium hydride and 1 in DMF provides the desired arylalkylaryl ether 3. Reaction of aniline 4, prepared as described below, or thiophenol 6, prepared as described in EPA 495 594, with sodium hydride and 1 in DMF produces arylalkylaryl amine 5, or arylalkylaryl thioether 7, respectively.

Scheme 1

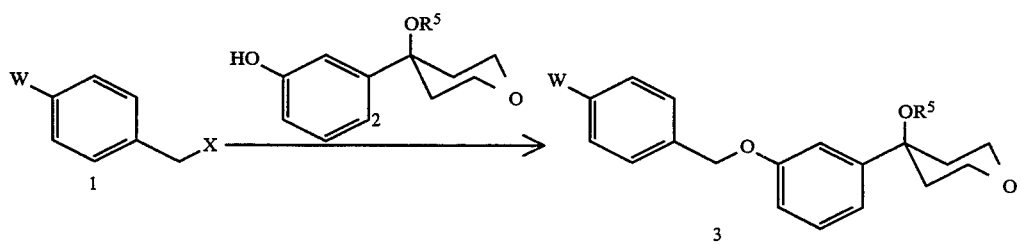

-continued
Scheme 1

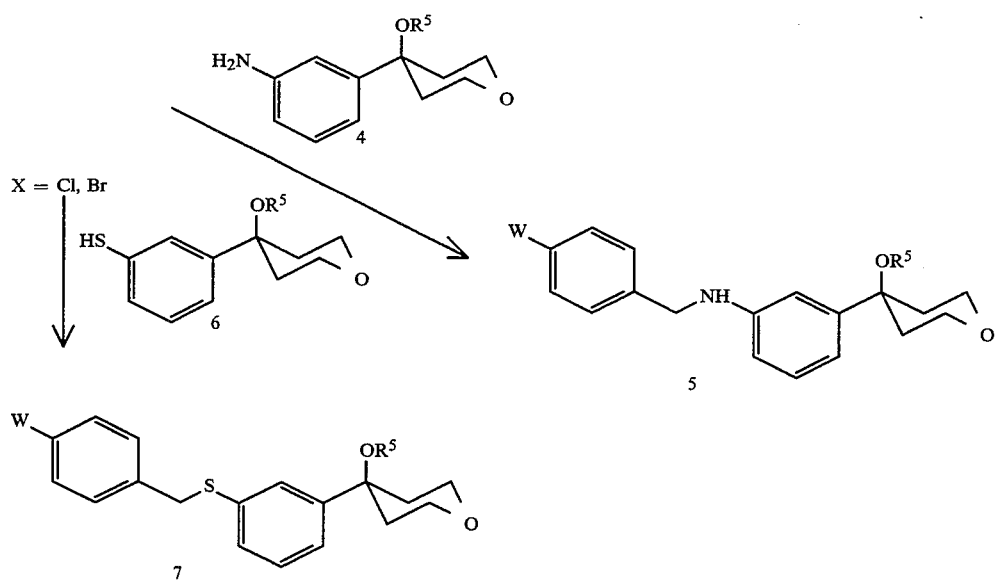

The preparation of compounds where $R^6$ is alkyl is shown in Scheme 2. 4-aminobenzyl alcohol is reacted with tert-butyldimethylsilyl chloride to form 9, which is then diacylated by treatment sodium acetate and acetic anhydride according to the method of Corley, R. S. and Blout, E. R., J. Am. Chem. Soc. 1947, 69, 755, 761 to form 10. Conversion of 10 to the bromide is accomplished as described by Aizupurua, J. M., Cossio, F. P., and Paloma, C., J. Org. Chem. 1986, 51,4941. Arylalkylaryl ether 12 is then prepared from bromide 11 as described in scheme 1. Treatment of 12 with one equivalent of LiOH results in removal of one acetyl group to form 13, which is then alkylated by treatment with NaH and the desired alkyl halide to form 14. The second acyl group is removed by treatment of 14 with KOH to form key intermediate 15, which can be reacted with trimethylsilylisocyanate to form 16, or deprotonated with an alkyllithium reagent and acylated with the desired carbamyl chloride to form 17.

Scheme 2

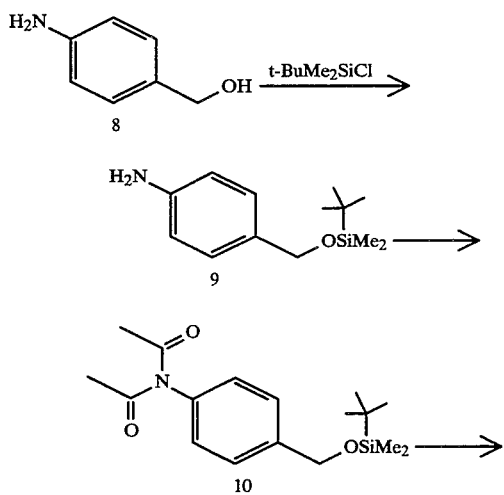

-continued
Scheme 2

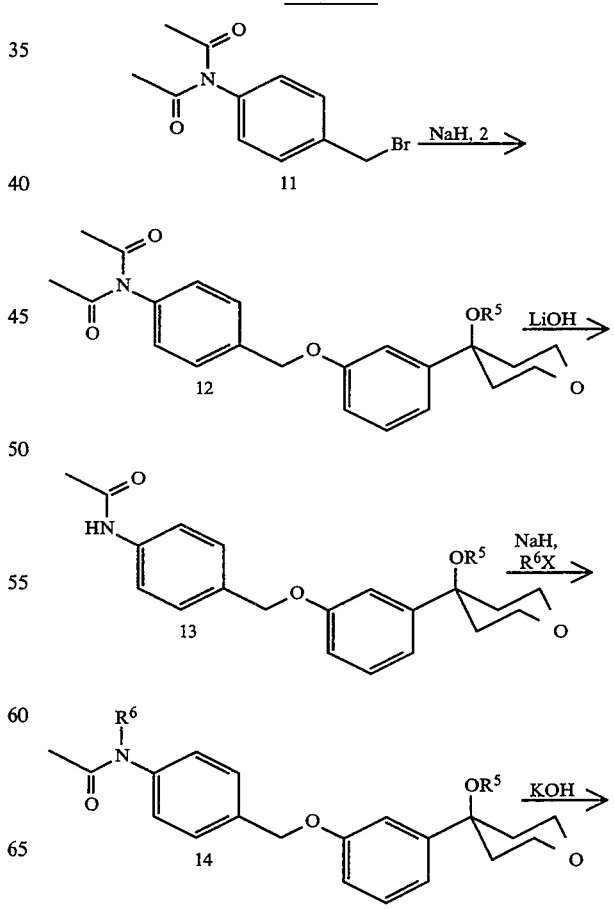

Scheme 2 -continued

Scheme 3

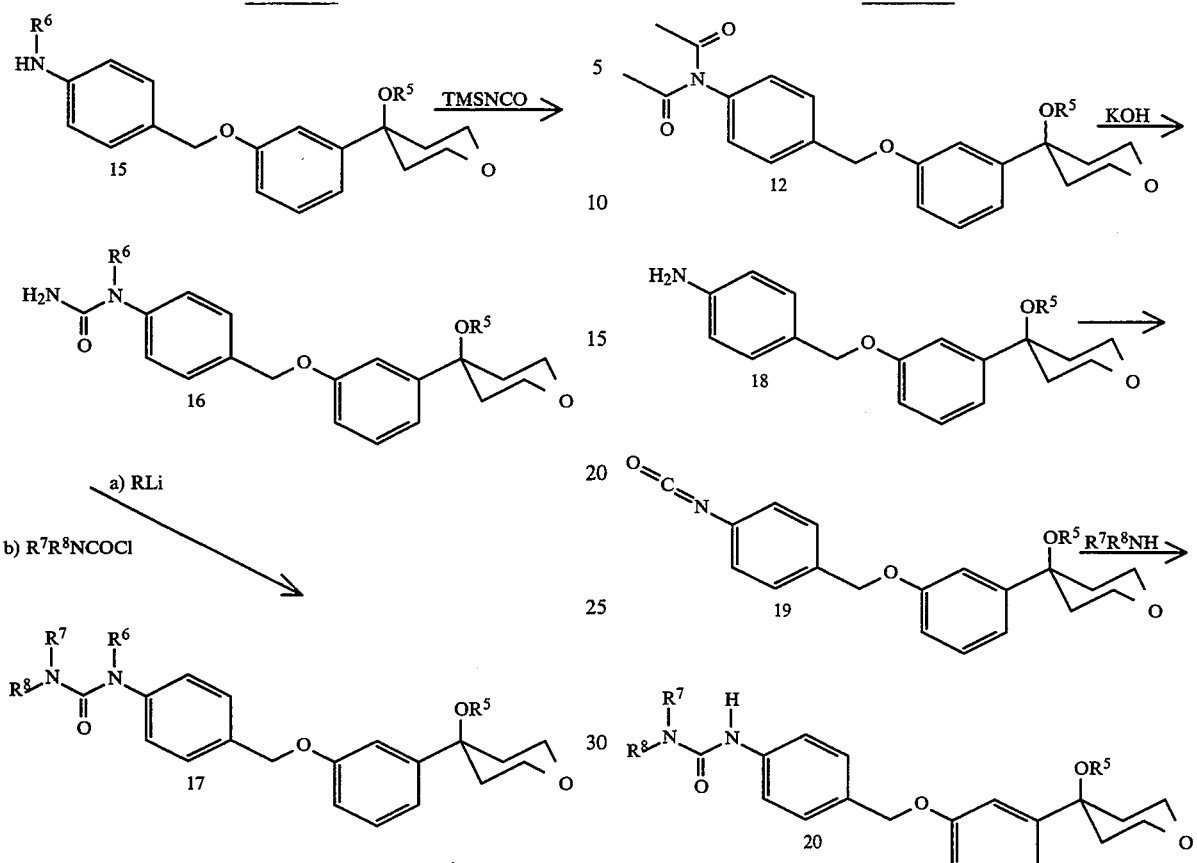

The preparation of compounds where $R^6$ is H is outlined in Scheme 3. Reaction of diacyl compound 12 with KOH produces amine 18 which is then treated with triphosgene to form isocyanate 19. Reaction of 19 with the desired amine produces 20.

The preparation of the compounds of this invention where $R^8$ is haloalkyl, or aminoalkyl is shown in Scheme 4a. Amine 15, prepared as in scheme 3, is treated with the desired haloalkylisocyanate to form haloalkyl derivative 21. Conversion of 21 to azide 22, followed by reduction of the azide with 1,3-propanedithiol provides aminoalkyl derivative 23. Compounds in which $R^7$ is alkyl are prepared by alkylation of 22 followed by reduction with propanedithiol as described above.

Scheme 4a

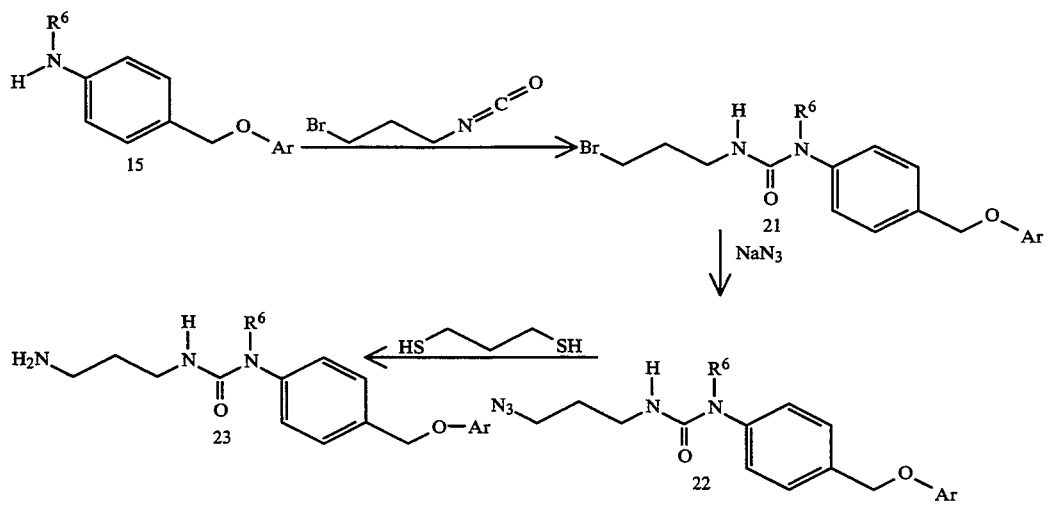

-continued
Scheme 4a

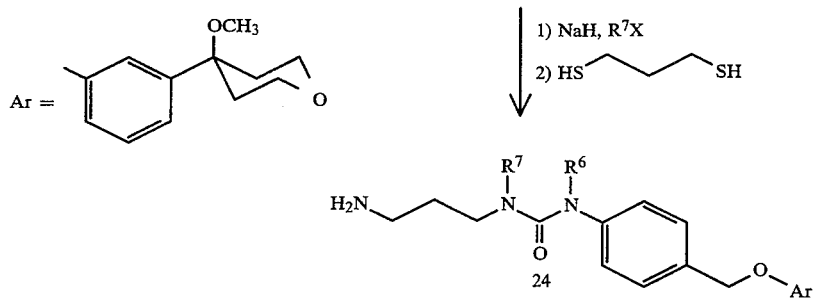

The preparation of the compounds of this invention where R⁸ is hydroxyalkyl, carboxyalkyl, (alkoxycarbonyl)alkyl, or (alkylaminocarbonyl)alkyl, is shown in Scheme 4b. Amine 15 is treated with an alkoxycarbonylalkylisocyanate to provide the alkoxycarbonylalkyl derivative 25, which can be alkylated by treatment with NaH and R⁷X. Hydrolysis of the ester provides (alkoxycarbonyl)alkyl derivative 27, and reduction of 26 with lithium borohydride or 27 with BH₃ provides the hydroxyalkyl compound 28. Ester 25 is hydrolyzed or reduced as described above to prepared the derivatives wherein R⁷ is H. The (alkylaminocarbonyl)alkyl derivatives are prepared from esters 25 and 26, or acids 27 and 29 by standard synthetic methods.

Scheme 4b

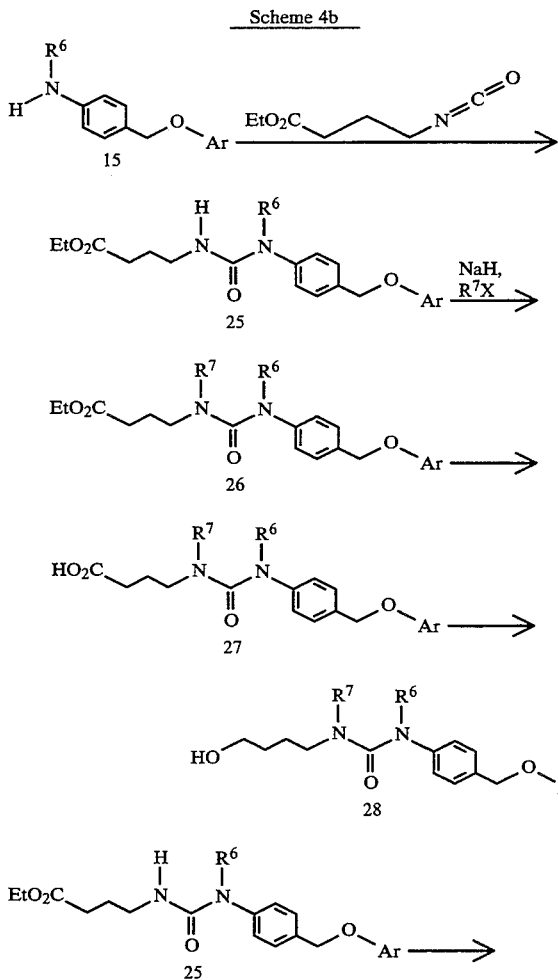

-continued
Scheme 4b

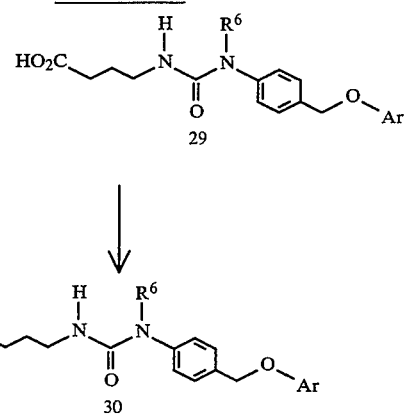

The preparation of the arylpropynyl-, arylpropenyl-, and arylpropyl-aryl ethers is shown in Scheme 5. 4-iodoaniline is convened to urea 31 by acylation with dimethylcarbamyl chloride, followed by alkylation with NaH and MeI. Coupling of 31 with propargyl alcohol provides propynol 32 which is convened to chloride 31 by treatment with phosphorus trichloride. The desired arylpropynyl-aryl ether 34 is prepared as described in scheme 1.

Treatment of alkynol 32 with Red-Al (sodium bis(2-methoxyethoxy)aluminum hydride) and conversion of the resulting allylic alcohol to the bromide with phosphorus tribromide provides 33, which is convened to the desired arylpropenyl-aryl ether 34 as described in scheme 1. Catalytic hydrogenation of 13 provides saturated compound 35.

Scheme 5

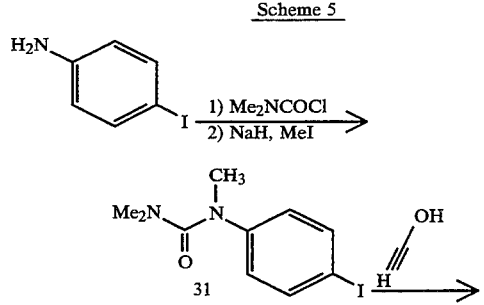

Scheme 5
-continued

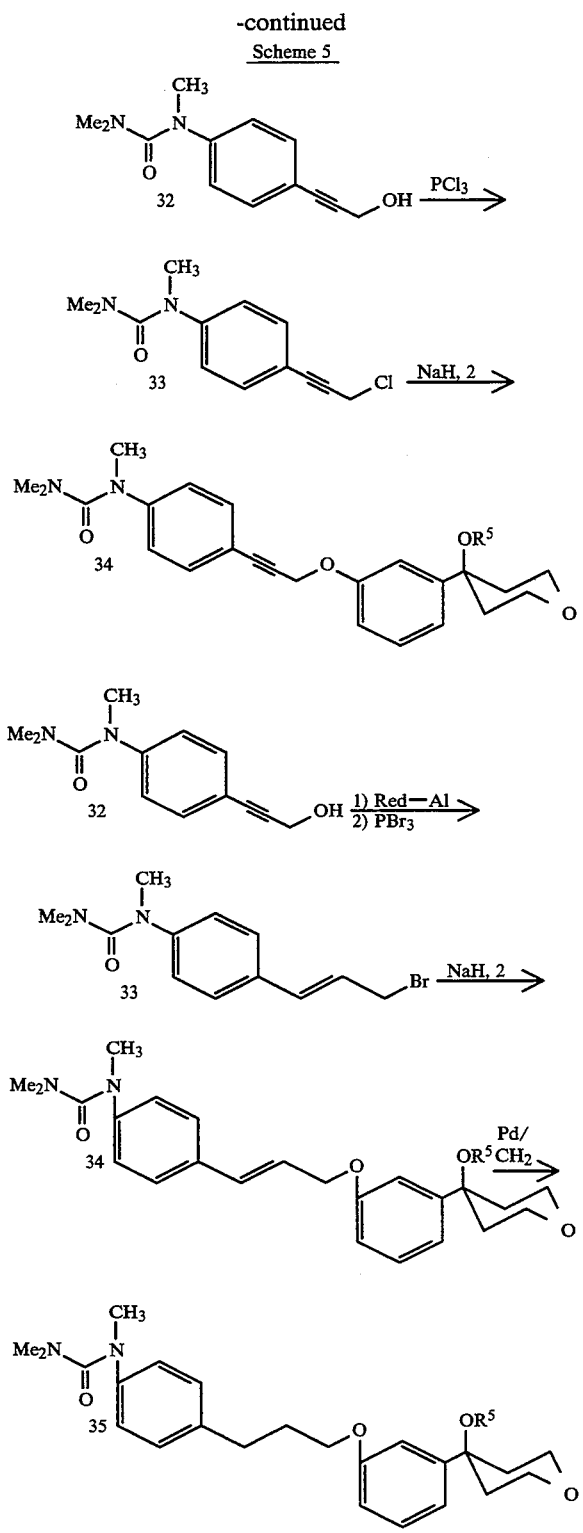

In a preferred embodiment, shown in Scheme 6, aminobenzoic acid 36 is treated with methyl isocyanate to form urea 37. Treatment of 37 with excess NaH and iodomethane produces trimethyl urea 38, which is reduced to benzylic alcohol 39 by treatment with lithium triethylborohydride. Conversion to the benzyl halide and displacement with 2 is accomplished as described in scheme 1.

Scheme 6

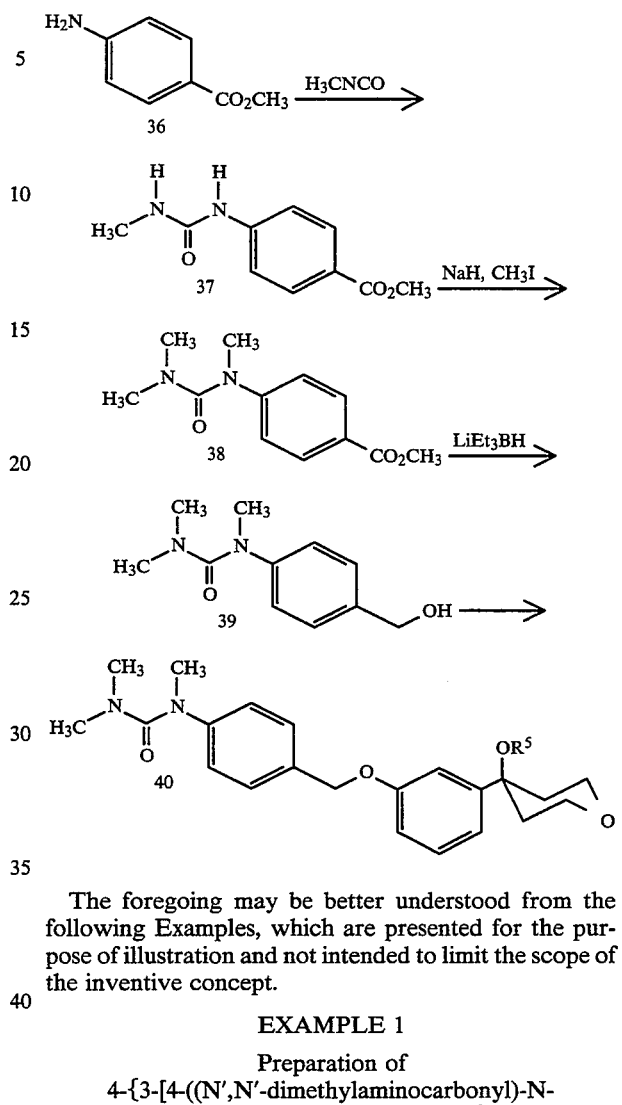

The foregoing may be better understood from the following Examples, which are presented for the purpose of illustration and not intended to limit the scope of the inventive concept.

EXAMPLE 1

Preparation of 4-{3-[4-((N',N'-dimethylaminocarbonyl)-N-methylamino)benzyloxy]-5-fluorophenyl}-4-methoxytetrahydropyran Step 1. Preparation of methyl 4-(N-methylaminocarbonyl)aminobenzoate.

A solution of methyl 4-aminobenzoate (15 g, 99 mmol), and methyl isocyanate (11.8 mL, 200 mmol) in toluene (400 mL) was heated at 100° C. under $N_2$ for 3 hours during which time a precipitate formed slowly. Additional methyl isocyanate (11.8 mL, 200 mmol) was added and heating was continued for 2 hours. The reaction mixture was cooled to 0° C. and filtered. The precipitate was washed with ether and vacuum-dried to give methyl 4-(N-methylaminocarbonyl)aminobenzoate as a colorless solid (17.5 g, 85%).

Step 2. Preparation of methyl 4-[(N',N'-dimethylaminocarbonyl)-N-methylamino]benzoate.

To a 0° C. suspension of NaH (80% oil dispersion, 3.60 g, 120 mmol) in THF (200 mL) under $N_2$ was added a solution of methyl 4-(N-methylaminocarbonyl)aminobenzoate (10.0 g, 48 mmol), prepared as in step 1, in THF (40 mL). The reaction mixture was stirred at 0° C. until gas evolution ceased, then the cold bath was removed and stirring was continued for 1.5 hours. A solution of iodomethane (6.6 mL, 106 mmol) in DMF (24 mL) was added and the reaction mixture was stirred for 72 hours at ambient temperature. NaH (2.0 g), and iodomethane (5.0 mL) were then added and the reaction mixture was stirred for an additional 2 hours. The reaction mixture was poured slowly into ice-water and the organics were stripped off in vacuo. The aqueous solution was extracted with ethyl acetate (10 x). The combined organic layers were dried over MgSO$_4$, filtered, and concentrated. Pure methyl 4-[(N',N'-dimethylaminocarbonyl)-N-methylamino]benzoate (6.62 g, 58%) was obtained as a colorless oil which crystallized on standing after chromatography on silica gel ( 40%, then 50% ethyl acetate/hexanes). mp 71°–73° C.

Step 3. Preparation of 4-[(N',N'-dimethylaminocarbonyl)-N-methylamino]benzyl alcohol.

To a 0° C. solution of methyl 4-[(N',N'-dimethylaminocarbonyl)-N-methylamino]benzoate (1.50 g, 6.35 mmol), prepared as in step 2, in THF (11.4 mL) was added lithium triethylborohydride (1.0M solution in THF, 14 mmol). The reaction mixture was stirred for 1 hour. Water (3.0 mL) and H$_2$O$_2$ (30% aqueous solution, 5.0 mL) were added and the reaction mixture was stirred at 45° C. for 20 min. Aqueous HCL (6M, 8.0 mL) was added and the reaction mixture was stirred at reflux for 14 hours. The reaction mixture was cooled to ambient temperature and poured into ethyl acetate. The aqueous phase was extracted three times with ethyl acetate. The combined organic layers were dried over MgSO$_4$, filtered, and concentrated in vacuo. 4-[(N',N'-dimethylaminocarbonyl)-N-methylamino]benzyl alcohol (797 mg, 61%) was isolated as a colorless solid by chromatography on silica gel (ethyl acetate). mp 65°–66° C.

Step 4. Preparation of 4-[(N',N'-dimethylaminocarbonyl)-N-methylamino]benzyl chloride.

To a stirred solution at −23° C. under N$_2$ of 4-[(N',N'-dimethylaminocarbonyl)-N-methylamino]benzyl alcohol (77.0 mg, 0.37 mmol), prepared as in step 4, in dry CH$_2$Cl$_2$ (3.7 mL) was added triethylamine (67.0 μL, 0.48 mmol), and methanesulfonyl chloride (34.0 μL, 0.44 mmol). The reaction mixture was stirred at ambient temperature until TLC indicated complete reaction (∼5 hours). The resultant solution was poured into ethyl acetate and the organic phase was washed (2 X, water; 2 X, brine), dried (MgSO$_4$), filtered and concentrated in vacuo. Purification by flash chromatography on silica gel (70% ethyl acetate/hexane provided 4-[(N',N'-dimethylaminocarbonyl)-N-methylamino]-benzyl chloride (56.0 mg, 67.0%) as a colorless oil which crystallized on standing at −25° C. mp 38.5°–39° C. $^1$H NMR (300MHz, CDCl$_3$) δ7.34 (2H, d, J=8.5 Hz), 7.04 (2H, d, J=8.5 Hz), 4.57 (2H, s), 3.22 (3H, s), 2.71 (6H, s). MS m/e 227 (M+H)+, 244 (M+NH$_4$)+.

Step 5. Preparation of 4-{3-[4-((N',N'-dimethylaminocarbonyl)-N-methylamino)benzyloxy]-5-fluorophenyl}-4-methoxytetrahydropyran.

4-methoxy-4-(5-fluoro-phenoxy-3-yl)tetrahydropyran (58.0 mg, 0.26 mmol), prepared as described in EPA 375-404, was dissolved in dry DMF and sodium hydride (16.0 mg, 0.39 mmol) was added to the mixture. After gas evolution ceased, a solution of 4-[(N',N'-dimethylaminocarbonyl)-N-methylamino]benzyl chloride, (53.0 mg, 0.23 mmol) prepared as in step 4, in dry DMF (1.0 mL) was added. The reaction was stirred for 1 hour at ambient temperature and quenched by adding excess saturated aqueous ammonium chloride. The resulting biphasic mixture was poured into ethyl acetate and the organic phase was washed (1 X, saturated aqueous ammonium chloride; 2 X, brine), dried (MgSO$_4$), filtered and concentrated in vacuo to give an oil. Purification by flash chromatography on silica gel (50% ethyl acetate/hexane) provided 4-{3-[4-((N',N'-dimethylaminocarbonyl)-N-methylamino)benzyloxy]-5-fluorophenyl}-4-methoxytetrahydropyran as a colorless oil (34.0 mg, 35.0%). $^1$H NMR (300 MHz, CDCl$_3$) δ7.39 (2H, d, J=8.5 Hz), 7.08 (2H, d, J=8.5 Hz), 6.80 (1H, br s), 6.72 (1H, br dt, J=9.9, 1.9, 1.9 Hz), 6.63 ($^1$H, dt, J=9.9, 2.0, 2.0 Hz), 5.0 (2H, s), 3.87 to 3.68 (4H, m), 3.22 (3H, s), 2.98 (3H, s), 2.72 (6H, s), 2.03 to 1.85 (4H, m). MS m/e 417 (M+H)+, 434 (M+NH$_4$)+. Analysis calc'd for C$_{23}$H$_{29}$FN$_2$O$_4$: C, 66.33; H, 7.02; N, 6.73. Found: C, 66.27; H, 6,84; N, 6.71.

EXAMPLE 2

Preparation of 4-{3-[4-((N',N'-dimethylaminothiocarbonyl)-N-methylamino)benzyloxy]-5-fluorophenyl}-4-methoxytetrahydropyran.

The desired compound is prepared by treatment of 4-{3-[4-((N',N'-dimethylaminocarbonyl)-N-methylamino)benzyloxy]-5-fluorophenyl}-4-methoxytetrahydropyran, prepared as in Example 1 with Lawesson's Reagent ([2,4bis(4-methoxyphenyl)-1,3-dithia-2,4-diphosphetane-2,4-disulfide) according to the method of Katah, A., Kashima, C., and Omote, Y. Heterocycles, 1982, 19(12), 2283.

EXAMPLE 3

Preparation of 4-{3-[4-((N',N'-dimethylaminocarbonyl)-N-methylamino)benzyloxy]phenyl}-4-methoxytetrahydropyran The desired compound is prepared according to the method of Example 1, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 4

Preparation of 4-{3-[4-((N',N'-dimethylaminocarbonyl)-N-methylaminobenzyl)amino]phenyl]-4-methoxytetrahydropyran Step 1. Preparation of H-t-Boc-3-bromoaniline.

3-bromoaniline (10 g, 58.1 mmol) and di-tert-butyldicarbonate (19.0 g, 87.1 mmol) were dissolved in 2M aqueous sodium hydroxide and heated at reflux for 1 hour. After cooling to ambient temperature, the reaction mixture was extracted with ethyl acetate. The organic layer was washed (saturated aqueous ammonium chloride, 1x; water, 1x; and brine, 2x), dried (MgSO$_4$), filtered, concentrated in vacuo, and dried under high vacuum to provide N-t-Boc-3 bromoaniline as a colorless solid (15.8 g, 100%). mp 83° C. $^1$H NMR (300 MHz, CDCl$_{13}$) δ7.66 ($^1$H, br m), 7.08–7.23 (3H, m), 6.46 (1H, br s), 1.52 (9H, s). MS m/e 272/274 (M+H)+, 289/291 (M+NH$_4$)+.

Step 2. Preparation of 4-(3-t-butyloxycarbonylaminophenyl)-4-hydroxytetrahydropyran.

A flask charged with N-t-Boc-3 bromoaniline (6.0 g, 22.0 mmol), prepared as in step 1, THF (88 mL), and a magnetic stirbar was cooled to −78° C. under a flow of nitrogen. To this solution was added n-butyllithium (22 mL of 2.5M solution in hexanes, 55.1 mmol) in a dropwise hshion from a syringe. The resulting solution was stirred at −78° C. for 1.5 hours. Tetrahydro-4H-pyran-4-one (2.5 mL, 26.5 mmol) was added neat to the solution, the cooling bath was removed, and the resulting solution was stirred at ambient temperature for 0.5 hours. The reaction was quenched carefully by adding excess saturated aqueous ammonium chloride. The mixture was partitioned between ethyl acetate and saturated aqueous ammonium chloride. The organic layer was washed (1 x, saturated aqueous ammonium chloride; 2x, water, 1x, brine), dried (MgSO$_4$), and concentrated in vacuo to provide a solid. Recrystallization from chloroform/hexanes provided 4-(3-t-butyloxycarbonylaminophenyl)-4-hydroxytetrahydropyran as a beige solid (4.31 g, 67%). mp 140°–142° C. $^1$H NMR (300 MHz, CDCl$_3$) δ7.55 (1H, br m), 7.21–7.32 (2H, m), 7.14 (1H, dt, J=7, 1, 1 Hz), 6.52 ($^1$H, br s), 3.93 (2H, td, J=12, 12, 2.5 Hz), 3.87 (2H, ddd, J=12, 6, 2 Hz), 2.19 (2H, ddd, J=13.5, 12.5, 6 Hz), 1.69 (2H, br t, J=13.5 Hz), 1.52 (9H, s); MS m/e 293 (M+NH$_4$-H$_2$O)+, 311 (M+NH$_4$)+.

Step 3. Preparation of 4-(3-aminophenyl)-4,hydroxytetrahydropyran.

To an ice-cooled solution of 4-(3-t-butyloxycarbonylaminophenyl)-4-hydroxytetrahydropyran (2.0 g, 6.8 mmol), prepared as in step 2, in dichloromethane (14 mL) was added trifluoroacetic acid (14, mL). The resulting solution was stirred for 0.25 hours at 0° C. and 1 hour at ambient temperature. The volatiles were removed in vacuo and the resulting solution was basified with saturated aqueous potassium carbonate. The resulting mixture was diluted with dichloromethane and the layers separated. The aqueous layer was extracted (4x, dichloromethane). The combined organic layers were dried (MgSO$_4$), and concentrated in vacuo to provide a solid. Trituration with hexanes provided 4-(3-aminophenyl)-4-hydroxytetrahydropyran as a colorless solid (1.01 g, 77%). mp 154°–155° C. $^1$H NMR (300 MHz, CDCl$_{13}$) δ7.17 (1H, dt, J=7.5 ,1 Hz), 6.84–6.88 (2H, m), 6.62 Hz), (1H, br d, J=7.5 Hz), 3.93 (2H, td, J=12, 12, 2.5 Hz), 3.84 (2H, ddd, J=12, 5, 1.5 2.05–32 (4H, m). MS m/e 193 (M+NH$_4$-H$_2$O)+, 211 (M+NH$_4$)+.

Step 4. Preparation of 4-(3-aminophenyl)-4-methoxytetrahydropyran.

To a solution of 4-(3-aminophenyl)-4-hydroxytetrahydropyran (630 mg, 3.26 mmol), prepared as in step 3, in dry DMF (13 mL) was added sodium hydride (326 mg of a 60% oil dispersion). The reaction was stirred at ambient temperature for 1 hour and then methyl iodide (0.24 mL, 3.19 mmol) was added neat. The resulting solution was stirred at ambient temperature for 0.5 hour and quenched with saturated aqueous ammonium chloride. The biphasic solution was extracted with ethyl acetate. The organic layer was washed (1x, saturated aqueous ammonium chloride; 2x, brine), dried (MgSO$_4$), and concentrated in vacuo to provide an oil. Chromatography on silica gel with 20% ethyl acetate/hexanes as the eluant provided 4-(3-aminophenyl)-4-methoxytetrahydropyran as a beige solid (510 mg, 76%). mp 99.0°–100.5° C. $^1$H NMR (300 MHz, CDCl$_3$) δ7.17 (1H, t, J=9 Hz), 6.73–6.82 (2H, m), 6.62 (1H, ddd, J=9, 2, 1 Hz), 3.85 (2H, td, J=10.5, 10.5, 2.5 Hz), 3.81 (2H, ddd, J=10.5, 9, 3 Hz), 2.99 (3H, s), 1.87–2.07 (4H, m). MS m/e 207 (M)+, 225 (M+NH$_4$)+.

Step 5. Preparation of 4-{3-[4-((N′,N′-dimethylaminocarbonyl)-N-methylaminobenzyl)-amino]-phenyl}-4-methoxytetrahydropyran.

The desired compound is prepared according to the method of Example 1, step 5, except substituting 4-(3-aminophenyl)-4-methoxytetrahydropyran, prepared as in step 4, for 4-methoxy-4-(5-fluoro-phenoxy-3-yl)tetrahydropyran.

EXAMPLE 5

Preparation of 4-{3-[4-((N′,N′-dimethylaminothiocarbonyl)-N-methylaminobenzyl)amino]phenyl}-4-methoxytetrahydropyran The desired compound is prepared according to the method of Example 2, except substituting 4-{3-[4-((N′,N′-dimethylaminocarbonyl)-N-methylaminobenzyl)amino]phenyl}-4methoxytetrahydropyran, prepared as in Example 4, for 4-{3-[4-((N′,N′-dimethylaminocarbonyl)-N-methylamino)-benzyloxy]-5-fluoro-phenyl}-4-methoxytetrahydropyran.

EXAMPLE 6

Preparation of 4-{3-[4-((N′,N′-dimethylaminocarbonyl)-N-methylamino)benzylthio]phenyl}-4-methoxytetrahydropyran The desired compound is prepared according to the method of Example 1, except substituting 4-(3-thiophenyl)-4-methoxytetrahydrofuran, prepared as described in EPA 495 594, for 4-(5-fluoro-3-hydroxyphenyl)-4-methoxy-tetrahydropyran.

EXAMPLE 7

Preparation of 4-{3-[4-((N′,N′-dimethylaminocarbonyl)-H-methylamino)benzylthio]-5-fluorophenyl}-4-methoxytetrahydropyran The desired compound is prepared according to the method of Example 1, except substituting 4-(5-fluoro-3-thiophenyl)-4-methoxytetrahydrofuran, prepared as described in EPA 495 594, for 4-(5-fluoro-3-hydroxyphenyl)-4-methoxytetrahydropyran.

EXAMPLE 8

Preparation of 4-}3-[4-((N′,N′-dimethylaminocarbonyl)-N-methylamino)phenylthiol]phenyl}-4-methoxytetrahydropyran.

Step 1. Preparation of N-t-Boc-4-iodoaniline

The desired compound was prepared according to the method of Example 4, step 1, except substituting 4-iodoaniline for 3-bromoaniline. mp 140°–141° C. $^1$H NMR (300 MHz, CDCl$_3$) δ7.57 (2H, d, J=9 Hz), 7.13 (2H, d, J=9 Hz), 6.43 ($^1$H, br s), 1.52 (1H, br s). MS m/e 320 (M+H)+, 337 (M+NH$_4$)+.

Step 2, Preparation of 3-(4-aminophenylthio)bromobenzene.

A mixture of 3-bromothiophenol (3.00 g, 15.9 mmol), N-t-Boc-4-iodoaniline (5.00 g, 15.9 mmol), prepared as in step 1, CuI (756 mg, 4.00 mmol), and K$_2$CO$_3$ (4.40 g, 31.7 mmol) in DMF was heated at reflux under N$_2$ for 2 hours. The reaction mixture was poured into H$_2$O/ethyl acetate and filtered through a pad of celite. The organic phase was washed twice with saturated aqueous NH$_4$Cl , once with H$_2$O, and twice with brine, dried over MgSO$_4$, filtered, and concentrated in vacuo. Chromatography on silica gel (20% ethyl acetate/hexanes) provided 3-(4aminophenylthio)bromobenzene (1.56 g, 35%). $^1$H NMR (300 MHz, CDCl$_3$) δ7.32 (2H, dt, J=9, 2, 2 Hz), 7.18-7.24 (2H, m), 6.97-7.07 (2H, m), 6.69 (2H, dt, J=9, 2, 2 Hz), 3.85 (2H, br s). MS m/e 280/282 (M+H)$^+$, 297/299 (M+NH$_4$)$^+$.

Step 3. Preparation of 3-[4-((N',N'dimethylaminocarbonyl)amino)phenylthio]bromobenzene.

To a solution of 3-(4-aminophenylthio)bromobenzene (415 mg, 1.48 mmol) in CH$_2$Cl$_2$ (7.4 mL) was added triethylamine (0.31 mL, 2.22 mmol) and dimethylcarbamyl chloride (0.34 mL, 3.70 mmol). The reaction mixture was stirred for one hour at ambient temperature and then at reflux for 18 hours, at which time additional triethylamine (3.0 mL), and dimethylcarbamyl chloride (3.0 mL) were added. The reaction mixture was heated at reflux for one hour, then cooled to ambient temperature and poured into ethyl acetate. The solution was washed twice with H$_2$O, twice with brine, dried over MgSO$_4$, filtered, and concentrated in vacuo. Chromatography on silica gel (40% ethyl acetate/hexanes) provided 3-[4-((N',N'-dimethylaminocarbonyl)amino)-phenylthio]bromobenzene (362 mg, 70%) as a colorless oil. $^1$H NMR (300 MHz, CDCl$_{13}$) δ7.37-7.45 (4H, m), 7.23-7.28 (2H, m), 7.06-7.10 (2H, m), 6.38 (1H, br s), 3.07 (6H, s). MS m/e 353/353 (M+H)$^+$, 368/370 (M+NH$_4$)$^+$.

Step 4. Preparation of 3-[4-((N', N'-dimethylaminocarbonyl)-N-methylamino)phenylthio]bromobenzene.

To a solution of 3-[4-((N', N'-dimethylaminocarbonyl)amino)phenylthio]bromobenzene (100 mg, 0.285 mmol), prepared as in step 3, in DMF (2.8 mL) was added NaH (60% oil dispersion, 30.0 mg, 0.745 mmol). The reaction mixture was stirred at ambient temperature for one hour. Iodomethane (22.3 μL, 0.358 mmol) was added and the reaction mixture was stirred at ambient temperature for 17 hours. The reaction mixture was quenched with saturated aqueous NH$_4$Cl and poured into ethyl acetate. The organic phase was washed once with saturated aqueous NH$_4$Cl, once with H$_2$O, and twice with brine, dried over MgSO$_4$, filtered, and concentrated in vacuo. 3-[4-((N', N'-dimethylaminocarbonyl)-N-methylamino)phenylthio]bromobenzene (89.2 mg, 86% ) was obtained by chromatography on silica gel (40% ethyl acetate/hexanes). $^1$H NMR (300 MHz, CDCl$_3$) δ7.38 (2H, dt, J=9, 2, 2 Hz), 7.29-7.33 (2H, m), 7.13-7.16 (2H, m), 7.03 (2H, dt, J=9, 2, 2 Hz), 3.24 (3H, s), 2.75 (6H, s). MS m/e 365/367 (M+H)$^+$, 382/384 (M+NH$_4$)$^+$.

Step 5. Preparation of 4-{3-[4-((N',N'-dimethylaminocarbonyl)-N-methylamino)phenylthio]-phenyl}-4-hydroxytetrahydropyran.

The desired compound was prepared according to the method of Example 4, step 2, except substituting 3-[4-((N',N'-dimethylaminocarbonyl)-N-methylamino)-phenylthio]bromobenzene, prepared as in step 4 for N-t-Boc-3 bromoaniline, and substituting t-butyllithium for n-butyllithium. $^1$H NMR (300 MHz, CDCl$_{13}$) δ7.46 ($^1$H, m), 7.27-7.38 (4H, m), 7.17 (1H, dt, J=9, 2, 2 Hz), 7.01 (2H, dt, J=9,2,2 Hz), 3.82-3.95 (4H, m), 3.22 (3H, s), 2.73 (6H, s), 2.07-2.18 (2H, m), 1.58-1.73 (2H, m). MS m/e 386 (M-H$_2$O+NH$_4$)$^+$, 404 (M+NH$_4$)$^+$.

Step 6. Preparation of 4-{13-[4-((N',N'-dimethylaminocarbonyl)-N-methylamino)phenylthiol]-phenyl}-4-methoxytetrahydropyran.

The desired compound was prepared according to the method of Example 4, step 4, except substituting 4-{3-[4-((N',N'-dimethylaminocarbonyl)-N-methylamino)-phenylthio]phenyl}-4-hydroxytetrahydropyran for 4-(3-aminophenyl)-4-hydroxytetrahydropyran. $^1$H NMR (300 MHz, CDCl$_3$) δ7.30-7.36 (4H, m), 7.22-7.28 (1H, m), 7.18 (1H, dt, J=9,2,2 Hz), 7.01 (2H, dt, J=9,2,2 Hz), 3.77-3.89 (4H, m), 3.22 (3H, s), 2.96 (3H, s), 2.73 (6H, s), 1.86-2.04 (4H, m). MS m/e 401 (M+H)$^+$, 418 (M+NH$_4$)$^+$.

EXAMPLE 9

Preparation of 4-{3-[4-((N',N'-dimethylaminocarbonyl)-N-methylamino)phenylsulfinyl]phenyl}-4-methoxytetrahydropyran The desired compound is prepared by treatment of 4-{3-[4-((N',N'-dimethylaminocarbonyl)-N-methylamino)phenylthio]phenyl}-4-methoxytetrahydropyran, prepared as in Example 8, with sodium metaperiodate as described in EPA 409 413.

EXAMPLE 10

Preparation of 4-{3-[4-((N',N'-dimethylaminocarbonyl)-N-methylamino)phenylsulfonyl]phenyl}-4-methoxytetrahydropyran The desired compound is prepared by treatment of 4-{3-[4-((N',N'-dimethylaminocarbonyl)-N-methylamino)phenylthio]phenyl}-4methoxytetrahydropyran, prepared as in Example 8, with potassium peroxymonosulphate as described in EPA 409 413.

EXAMPLE 11

Preparation of 4-{3-[4-((N',N'-dimethylaminocarbonyl)aminomethyl)-benzyloxy]-5-fluorophenyl}-4-methoxytetrahydropyran.

Step 1. Preparation of 3-{[3-(4-bromomethyl)benzyloxy]-5-fluorophenyl}-4-methoxytetrahydropyran The desired compound was prepared according to the method of Example 1, step 5, except substituting α, α'-dibromo-p-xylene for 4-[(N',N'-dimethylaminocarbonyl)N-methylamino]benzyl chloride.

Step 2. Preparation of 4-{3-[4-((N',N'-dimethylcarbonyl)aminomethyl)benzyloxy]-5-fluorophenyl}-4-methoxytetrahydropyran.

To a solution of 1,1-dimethylurea (19 mg, 0.22 mmol), in DMF (1.0 mL), was added NaH (60% oil dispersion, 8.8 mg, 0.22 mmol). The reaction mixture was warmed to 50° C. and stirred for 0.5 hours. The reaction mixture was cooled to ambient temperature and a solution in DMF (1.0 mL), of 4-{3-[4-(bromomethyl)benzyloxy]-5-fluoro-phenyl}-4-methoxytetrahydropyran (90 mg, 0.22 mmol), prepared as in step 1, was added. The reaction mixture was stirred for four hours at ambient temperature, then H$_2$O (10 mL), and 1:1 ethyl acetate, pentane were added. The organic phase was washed with brine, dried over MgSO$_4$, filtered, and concentrated in vacuo. 4-{3-[(4-(N',N'-dimethylaminocarbonyl)aminomethyl)-benzyloxy]-5-fluorophenyl}-4-methoxytetrahydropyran (19 mg) was obtained by chromatography on silica gel (5% MeOH/CH$_2$Cl$_2$). $^1$H NMR (300 MHz, CDCl$_3$) δ7.30-7.45 (4H, m), 6.80 ($^1$H, t, J=1.5 Hz), 6.71 (1H, dt, J=10.5, 2.2, 2.2 Hz), 6.6 (1H, dt, J=10.5, 2.2, 2.2 Hz), 5.03 (2H, s), 4.65 ($^1$H, br s), 4.45 (2H, d, J=6 Hz), 3.79 to 3.85 (4H, m), 3.98 (3H, s), 3.93 (6H, s), 3.86 to 2.2 (4H, m). MS m/e 417 (M+H)$^+$, 434 (M+NH$_4$)$^+$.

EXAMPLE 12

Preparation of 4-{3-[4-((N',N'-dimethylaminocarbonyl)aminomethyl)-benzyloxy]-phenyl}-4-methoxytetrahydropyran The desired compound is prepared according to the method of Example 11, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 13

Preparation of 4-{3-[4-((N',N'-dimethylaminocarbonyl)aminomethyl)-benzylthio]-5-fluorophenyl}-4-methoxytetrahydropyran The desired compound is prepared according to the method of Example 11, except substituting 4-(5-fluoro-3-thiophenyl)-4-methoxytetrahydrofuran, prepared as described in EPA 495 594, for 4-methoxy-4-(5-fluorophenoxy-3-yl)tetrahydropyran.

EXAMPLE 14

Preparation of 4-{3-[4-((N',N'-dimethylaminocarbonyl)aminomethyl)-benzylthio]phenyl}-4-methoxytetrahydropyran The desired compound is prepared according to the method of Example 12, except substituting 4-(3-thiophenyl)-4-methoxytetrahydrofuran, prepared as described in EPA 495 594, for 4-(5-fluoro-3-thiophenyl)-4-methoxytetrahydrofuran.

EXAMPLE 15

Preparation of 4-{3-[4-((N',N'-dimethylaminocarbonyl)aminomethyl-benzyl)amino]phenyl}-4-methoxytetrahydropyran The desired compound is prepared according to the method of Example 11, except substituting 4-(3-aminophenyl)-4-methoxytetrahydropyran, prepared as in Example 4, for 4-methoxy-4-(5-fluoro-phenoxy-3-yl)tetrahydropyran.

EXAMPLE 16

Preparation of 4-{3-[4-(((N',N'-dimethylaminocarbonyl)-N-methylamino)methyl)benzyloxy]-5-fluorophenyl}-4-methoxytetrahydropyran The desired compound is prepared according to the method of Example 1, step 2, except substituting 4-{3-[4-((N',N'-dimethylaminocarbonyl)aminomethyl)benzyloxy]-5-fluoro-phenyl}-4-methoxytetrahydropyran, prepared as in Example 11, for 4-[(N', N'-dimethylaminocarbonyl)amino]benzoate.

EXAMPLE 17

Preparation of 4-{3-[4-(imidazolidin-2-on-1-ylmethyl)benzyloxy]-5-fluorophenyl}-4-methoxytetrahydropyran The desired compound was prepared according to the method of Example 11, step 2, except substituting 2-imidazolidinone for 1,1-dimethylurea. $^1$H NMR (300 MHz, CDCl$_{13}$) $\delta$7.41(2H, d, J=9 Hz ),7.32 (2H, d, J=9 Hz), 6.81 (1H, t, J=1.5 Hz), 6.71 (1H, dq, J=10.5, 1.5, 1.5 Hz), 6.61 (1H, dt, J=10.5, 3, 3 Hz), 5.04 (2H, s), 4.39 (2H, s), 4.35 (1H, br s), 3.71 to 3.86 (4H, m), 3.28–3.35 (4H, m), 2.98 (3H, s), 1.85 to 2.05 (4H, m). MS m/e 415 (M+H)$^+$, 432 (M+NH$_4$)$^+$.

EXAMPLE 18

Preparation of 4-{3-[4-(imidazolidin-2-on-1-ylmethyl)benzyloxy]-phenyl}-4methoxytetrahydropyran The desired compound is prepared according to the method of Example 17, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 19

Preparation of 4-{3-[4-(imidazolidin-2-on-1-ylmethyl)benzylthio]-5-fluorophenyl}-4-methoxytetrahydropyran The desired compound is prepared according to the method of Example 17, except substituting 4-(5-fluoro-3-thiophenyl)-4-methoxytetrahydrofuran, prepared as described in EPA 495 594, for 4-methoxy-4-(5-fluorophenoxy-3-yl)tetrahydropyran.

EXAMPLE 20

Preparation of 4-{3-[4-(imidazolidin-2-on-1-ylmethyl)benzylthio]phenyl-4-methoxytetrahydropyran The desired compound is prepared according to the method of Example 19, except substituting 4-(3-thiophenyl)-4-methoxytetrahydrofuran, prepared as described in EPA 495 594, for 4-(5-fluoro-3-thiophenyl)-4-methoxytetrahydrofuran.

EXAMPLE 21

Preparation of 4-{3-[3-((N'N'-dimethylaminocarbonyl)-N-methylamino)benzyloxy]-5-fluorophenyl}-4-methoxytetrahydropyran Step 1. Preparation of 3-(O-t-butyldimethylsilyloxymethyl)aniline.

To a solution of 3-aminobenzyl alcohol (2.00 g, 16.2 mmol) and tertbutyldimethylsilyl chloride (2.90 g, 19.4 mmol) in CH$_2$Cl$_2$ (32.5 mL) was added triethylamine (7.45 mL, 53.5 mmol). The reaction mixture was stirred for 18 hours at ambient temperature and was then partitioned between ethyl acetate and H$_2$O. The organic phase was washed twice with H$_2$O, twice with brine, dried over MgSO$_4$, filtered, and concentrated in vacuo. 3-(O-t-butyldimethylsilyloxymethyl)aniline (2.18 g, 57%) was obtained as a yellow oil by chromatography on silica gel (30% ethyl acetate/hexane). $^1$H NMR (300 MHz, CDCl$_3$) $\delta$7.10 (1H, t, J=7.5 Hz), 6.67–6.72 (2H, m), 6.56 (1H, br d, J=7.5 Hz), 4.66 (2H, s), 3.63 (2H, br s), 0.94 (9H, s), 0.09 (6H, s). MS m/e 238(M+H)$^+$, 255 (M+NH$_4$)$^+$.

Step 2. Preparation of O-t-butyldimethylsilyl-3-[(N'-methylaminocarbonyl)amino]benzyl alcohol.

To a solution under N$_2$ of 3-(O-t-butyldimethylsilyloxymethyl)aniline (900 mg, 3.79 mmol) in toluene (7.6 mL) was added methylisocyanate (0.45 mL, 7.58 mmol). The reaction mixture was stirred at 100° C. for 1.5 hours and was then cooled to ambient temperature and partitioned between ethyl acetate and H$_2$O. The organic phase was washed once with H$_2$O, twice with brine, dried over MgSO$_4$, filtered, and concentrated in vacuo. The oily residue crystallized on standing. The crystalline solid was washed twice with hexane to provide O-t-butyldimethylsilyl-3-[(N'-methylaminocarbonyl)amino]benzyl alcohol (641 mg, 57%). mp 110°–113° C. $^1$H NMR (300 MHz, CDCl$_3$) δ7.23–7.28 (2H, m), 7.17 (1H, d, J=7.5 Hz), 7.03 (1H, d, J=7.5 Hz), 6.68 (1H, br s), 5.0 (1H, br q, J=4 Hz), 4.69 (2H, s), 2.80 (3H, d, J=5 Hz), 0.93 (9H, s), 0.09 (6H, s). MS m/e 295(M+H)+, 312 (M+NH$_4$)+.

Step 3. Preparation of O-t-butyldimethylsilyl-3-[(N'-N'-dimethylaminocarbonyl)-N-methylamino]benzyl alcohol.

The desired compound was prepared according to the method of Example 1, step 2, except substituting O-t-butyldimethylsilyl-3-[(N'methylaminocarbonyl)amino]benzyl alcohol, prepared as in step 2, for methyl 4-(N-methylaminocarbonyl)aminobenzoate. $^1$H NMR (300 MHz, CDCl$_3$) δ7.27 (1H, t, J=7.5 Hz), 7.00–7.06 (2H, m), 6.92 (1H, br d, J=7.5 Hz), 4.71 (2H, s), 3.21 (3H, s), 2.68 (6H, s),0.93 (9H, s), 0.09 (6H, s); MS m/e 323 (M+H)+; 340 (M+NH$_4$)+.

Step 4. Preparation of 3-[(N'-N'-dimethylaminocarbonyl)-N-methylamino]benzyl bromide.

To a solution of O-t-butyldimethylsilyl-3-[(N'-N'-methylaminocarbonyl)-N-methylamino]benzyl alcohol (371 mg, 1.15 mmol) in CH$_2$Cl$_2$ (5.7 mL) was added a solution of dibromotriphenylphosphorane (1.45 g, 3.45 mmol) in CH$_2$Cl$_2$ (5.7 mL). The reaction mixture was stirred for stirred for 1.5 hours at ambient temperature and was then partitioned between ethyl acetate and H$_2$O. The organic phase was washed twice with H$_2$O, twice with brine, dried over MgSO$_4$, filtered, and concentrated in vacuo. Pure 3-[(N'-N'-methylaminocarbonyl)-N-methylamino]benzyl bromide (282 mg, 90%) was obtained by chromatography on silica gel. $^1$H NMR (300 MHz, CDCl$_3$) δ7.29 (1H, t, J=7.5 Hz), 7.06–7.12 (2H, m), 6.98 (1H, br d, J=7.5 Hz), 4.46 (2H, s), 3.21 (3H, s), 2.72 (6H, s),0.93 (9H, s), 0.09 (6H, s). MS m/e 271/273 (M+H)+, 288/290 (M+NH$_4$)+.

Step 5. Preparation of 4-{3-[3-((N',N'-dimethylaminocarbonyl)-N-methylamino)benzyloxy]-5-fluorophenyl}-4-methoxytetrahydropyran.

The desired compound was prepared according to the method of Example 1, step 5, except substituting 3-[(N'-N'methylaminocarbonyl)-N-methylamino]benzyl bromide, prepared as in step 4, for 4-[(N',N'-dimethylaminocarbonyl)-N-methylamino]benzyl chloride. $^1$H NMR (300 MHz, CDCl$_3$) δ7.34 (1H, t, J=7.5 Hz), 7.10–7.16 (2H, m), 7.02 (1H, br s, J=7.5 Hz), 6.81 (1H, br s), 6.72 (1H, br dt, J=9.9, 1.5, 1.5 Hz), 6.58 (1H, dt, J=9.9, 1.5, 1.5 Hz), 5.03 (2H, s), 3.80–3.86 (4H, m), 3.23 (3H, s), 2.98 (3H, s),2.68 (6H, s), 1.84–2.04 (4H, m). MS m/e 417 (M+H)+; 434 (M+NH$_4$)+. Analysis calc'd for C$_{23}$H$_{29}$FN$_2$O$_4$F: C, 66.33; H, 7.02; N, 6.73. Found C, 66.47; H, 7.01; N, 6.96.

EXAMPLE 22

Preparation of 4-{3-[3-((N',N'-dimethylaminocarbonyl)-N-methylamino)benzyloxylphenyl}-4-methoxyetrahydropyran The desired compound is prepared according to the method of Example 21, except substituting 4-(3-hydroxyphenyl)-4-methoxytetrahydrofuran, prepared as described in EPA 375 404, for 4-(5-fluoro-3-hydroxyphenyl)-4-methoxytetrahydropyran.

EXAMPLE 23

Preparation of 4-{3-[3-((N',N'-dimethylaminocarbonyl)-N-methylaminobenzyl)amino}-4-methoxytetrahydropyran The desired compound is prepared according to the method of Example 4, except substituting 3-[(N'-N'-methylaminocarbonyl)-N-methylamino]benzyl bromide, prepared as in Example 21, step 4, for 4-[(N',N'-dimethylaminocarbonyl)-N-methylamino]benzyl chloride.

EXAMPLE 24

Preparation of 4-{3-[3-((N',N'-dimethylaminocarbonyl)-N-methylamino)benzylthio]phenyl}-4-methoxytetrahydropyran The desired compound is prepared according to the method of Example 21, except substituting 4-(3-thiophenyl)-4-methoxytetrahydrofuran, prepared as described in EPA 495 594, for 4-( 5-fluoro-3-hydroxyphenyl)-4-methoxy-tetrahydropyran.

EXAMPLE 25

Preparation of 4-{3-[3-((N',N'-dimethylaminocarbonyl)-N-methylamino)benzylthio]-5-fluorophenyl}-4-methoxytetrahydropyran The desired compound is prepared according to the method of Example 21, except substituting 4-(5-fluoro-3-thiophenyl)-4-methoxytetrahydrofuran, prepared as described in EPA 495 594, for 4-(5-fluoro-3-hydroxyphenyl)-4-methoxytetrahydropyran.

The compounds represented in Table 2 are prepared by treatment of arylalkylamine 15 with trimethylsilylisocyanate, with R$^8$NCO, or with RLi and R$^7$R$^8$NCOCl as described in Scheme 2.

TABLE 2

Novel N-alkylurea inhibitors of 5-lipoxygenase

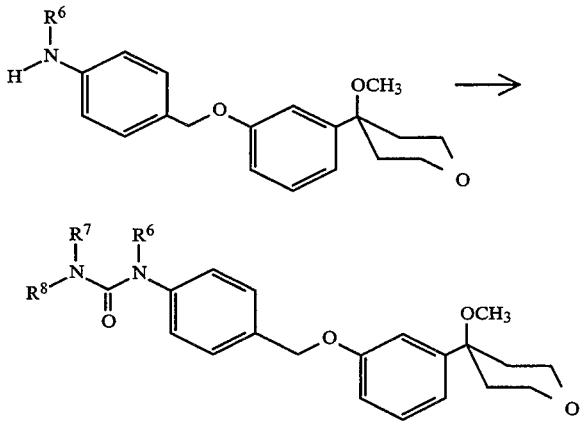

| Example | R$^6$ | R$^7$ | R$^8$ |
|---|---|---|---|
| 26 | Me | H | H |
| 27 | Me | H | Me |
| 28 | Me | H | Et |
| 29 | Me | H | Pr |
| 30 | Me | H | Bu |
| 31 | Me | Et | Me |
| 32 | Me | Pr | Me |
| 33 | Me | Bu | Me |
| 34 | Me | Et | Et |

TABLE 2-continued
Novel N-alkylurea inhibitors of 5-lipoxygenase

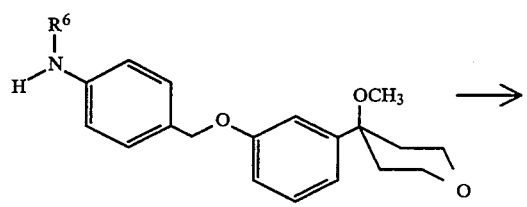

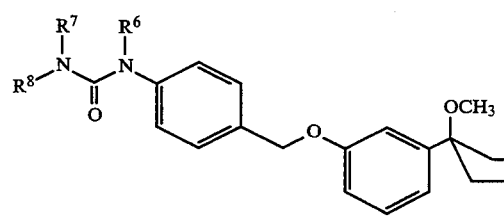

| Example | R⁶ | R⁷ | R⁸ |
|---|---|---|---|
| 35 | Me | Pr | Pr |
| 36 | Me | Bu | Bu |
| 37 | Me | Ph | H |
| 38 | Me | Ph | Me |
| 39 | Me | piperidinyl | |
| 40 | Me | morpholinyl | |
| 41 | Me | thiomorpholinyl | |
| 42 | Me | N-methylpiperazinyl | |
| 43 | Me | piperazinyl | |
| 44 | Et | H | Me |
| 45 | Et | Me | Me |
| 46 | Pr | H | Me |
| 47 | Pr | Me | Me |
| 48 | Bu | H | Me |
| 49 | Bu | Me | Me |

The compounds represented in Table 3 are prepared by reaction of isocyanate 19 with HNR³R⁴ as described in Scheme 3.

TABLE 3
Novel urea inhibitors of 5-lipoxygenase

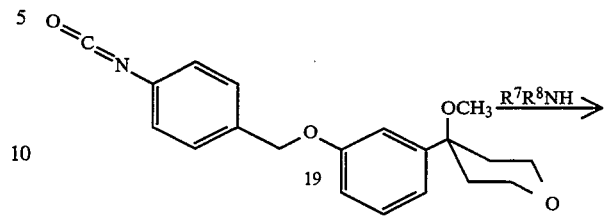

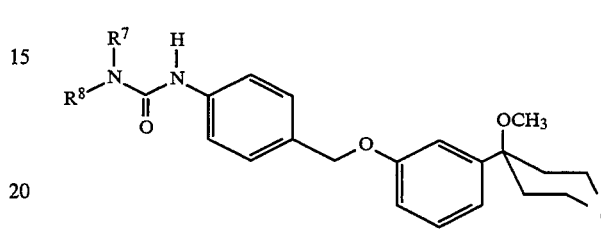

| Example | R⁷ | R⁸ |
|---|---|---|
| 50 | H | Me |
| 51 | H | Et |
| 52 | H | Pr |
| 53 | H | Bu |
| 54 | Me | Me |
| 55 | Me | Et |
| 56 | Me | Pr |
| 57 | Me | Bu |
| 58 | Et | Et |
| 59 | Pr | Pr |
| 60 | Bu | Bu |
| 61 | Ph | H |
| 62 | Ph | Me |
| 63 | piperidinyl | |
| 64 | morpholinyl | |
| 65 | thiomorpholinyl | |
| 66 | N-methylpiperazinyl | |
| 67 | piperazinyl | |

The compounds represented in Table 4 are prepared according to the method described in Schemes 4a and 4b.

TABLE 4

Novel haloalkyl-, hydroxyalkyl-, aminoalkyl-, (alkoxycarbonyl)alkyl-, carboxyalkyl-, and (aminoalkylcarbonyl)alkylurea derivatives of 5-Lipoxygenase.

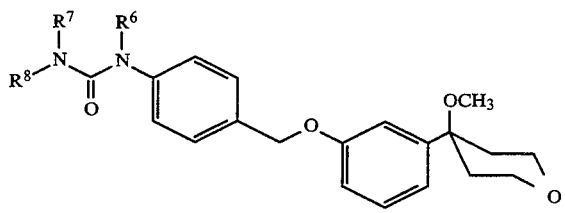

| Example | R⁶ | R⁸ | R⁷ |
|---|---|---|---|
| 68 | H | Br−(butyl) | H |
| 69 | H | Br−(butyl) | Me |
| 70 | H | H₂N−(butyl) | H |
| 71 | H | H₂N−(butyl) | Me |
| 72 | H | HO−(pentyl) | H |
| 73 | H | HO−(pentyl) | Me |
| 74 | H | HOOC−(butyl) | H |
| 75 | H | HOOC−(butyl) | Me |
| 76 | H | EtOOC−(butyl) | H |
| 77 | H | EtOOC−(butyl) | Me |
| 78 | H | CH₃NHC(O)−(butyl) | H |
| 79 | H | CH₃NHC(O)−(butyl) | Me |
| 80 | Me | Br−(butyl) | H |
| 81 | Me | Br−(butyl) | Me |
| 82 | Me | H₂N−(butyl) | H |
| 83 | Me | H₂N−(butyl) | Me |
| 84 | Me | HO−(pentyl) | H |
| 85 | Me | HO−(pentyl) | Me |

TABLE 4-continued

Novel haloalkyl-, hydroxyalkyl-, aminoalkyl-, (alkoxycarbonyl)alkyl-, carboxyalkyl-, and (aminoalkylcarbonyl)alkylurea derivatives of 5-Lipoxygenase.

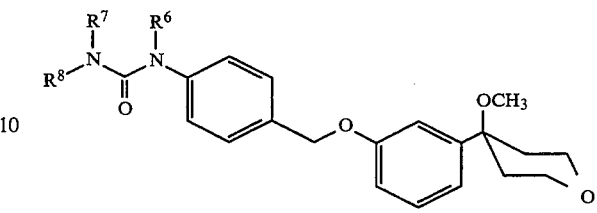

| Example | R⁶ | R⁸ | R⁷ |
|---|---|---|---|
| 86 | Me | HOOC−(butyl) | H |
| 87 | Me | HOOC−(butyl) | Me |
| 88 | Me | EtOOC−(butyl) | H |
| 89 | Me | EtOOC−(butyl) | Me |
| 90 | Me | CH₃NHC(O)−(butyl) | H |
| 91 | Me | CH₃NHC(O)−(butyl) | Me |

We claim:

1. A compound of the formula:

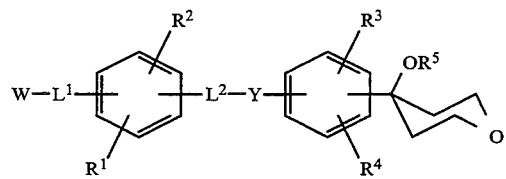

or a pharmaceutically acceptable salt thereof wherein
W is selected from the group consisting of

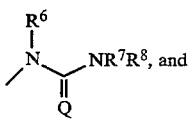 (a)

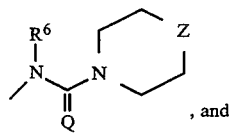 , and (b)

wherein
Q is oxygen or sulfur, $R^6$ and $R^7$ are independently selected from the group consisting of hydrogen and alkyl of one to four carbon atoms, provided that when $L^1$ is a valence bond, $R^6$ is alkyl of one to four carbon atoms, or $R^6$ and $R^7$, taken together with the nitrogen atoms to which they are attached, define a radical of the formula

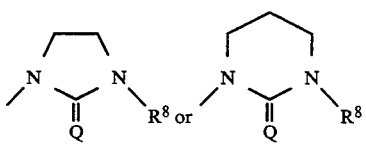

$R^8$ is selected from the group consisting of
hydrogen,
alkyl of one to four carbon atoms,
haloalkyl of one to four carbon atoms,
unsubstituted phenyl,
phenyl substituted with
alkyl of one to four carbon atoms,
alkoxy of one to four carbon atoms,
haloalkyl, or
halogen,
hydroxyalkyl of from one to four carbon atoms,
aminoalkyl of from one to four carbon atoms,
carboxyalkyl of from one to four carbon atoms,
(alkoxycarbonyl)alkyl where the alkyl and alkoxy portions each are of one to four carbon atoms,
(alkylaminocarbonyl)alkyl, where the alkyl and aminoalkyl portions each are of one to four carbon atoms; and Z is —CH2—, oxygen, sulfur, or —NR9 wherein R9 is hydrogen or alkyl of one to four carbon atoms;

$L^1$ is a valence bond or is selected from alkylene of one to three carbon atoms, propenylene, and propynylene;

$R^1$, $R^2$, $R^3$, and $R^4$ are independently selected from the group consisting of
alkyl of one to four carbon atoms,
alkoxy of one to four carbon atoms,
haloalkyl,
halogen,
cyano,
amino,
alkoxycarbonyl of one to four carbon atoms, and
dialkylaminocarbonyl where the alkyl portions are each of one to four carbon atoms;

$L^2$ is a valence bond or is selected from alkylene of one to three carbon atoms, propenylene, and propynylene;

Y is selected from the group consisting of
oxygen,
>NR10, where R10 is hydrogen or alkyl of one to four carbon atoms, and
where n=0, 1, or 2; and $R^5$ is alkyl of one to four carbon atoms.

2. A compound as defined by claim 1 of the formula:

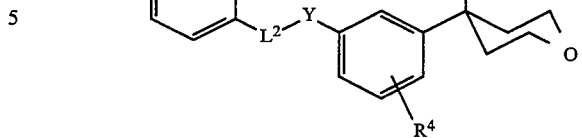

or a pharmaceutically acceptable salt thereof wherein W, $L^2$, y, $R^4$, and $R^5$ are defined therein.

3. A compound as defined by claim 2 wherein $L^2$ is methylene.

4. A compound as defined by claim 1 of the formula:

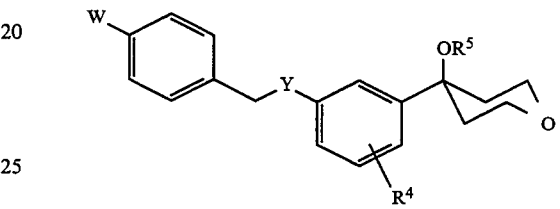

or a pharmaceutically acceptable salt thereof wherein W, Y, $R^4$, and $R^5$ are defined therein.

5. A compound or pharmaceutically acceptable salt thereof as defined in claim 4 wherein Y is oxygen.

6. A compound of pharmaceutically acceptable salt thereof as defined in claim 4 wherein Y is >NR10 wherein R10 is hydrogen or alkyl of one to four carbon atoms.

7. A compound of pharmaceutically acceptable salt thereof as defined in claim 4 wherein Y is

where n=0, 1, or 2.

8. A compound as defined by claim 1 of the formula:

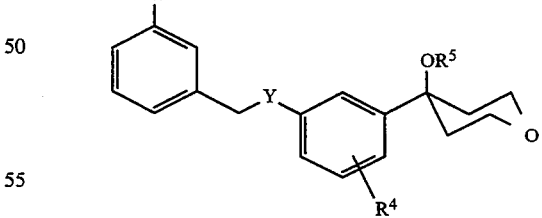

or a pharmaceutically acceptable salt thereof wherein W, Y, $R^4$, and $R^5$ are defined therein.

9. A compound of pharmaceutically acceptable salt thereof as defined in claim 8 wherein Y is oxygen.

10. A compound of pharmaceutically acceptable salt thereof as defined in claim 8 wherein Y is >NR10 wherein R10 is hydrogen or alkyl of one to four carbon atoms.

11. A compound or pharmaceutically acceptable salt thereof as defined in claim 8 wherein Y is $-\overset{(O)_n}{S}-$, where n=0, 1, or 2.

12. A compound as defined by claim 1 of the formula:

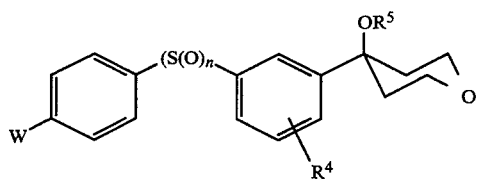

or a pharmaceutically acceptable salt thereof wherein W, n, $R^4$, and $R^5$ are defined therein.

13. A compound or pharmaceutically acceptable salt thereof as defined in claim 12 wherein n=0.

14. A compound selected from the group consisting of

4-{3-[4-((N',N'-dimethylaminocarbonyl)-N-methylamino)benzyloxy]-5-fluorophenyl}-4-methoxytetrahydropyran, 4-{3-[4-((N',N'-dimethylaminocarbonyl)-N-methylamino)phenylthio]phenyl}-4-methoxytetrahydropyran, 4-{3-[4-((N',N'-dimethylaminocarbonyl)aminomethyl)benzyloxy]-5-fluorophenyl}-4-methoxytetrahydropyran, 4-{3-[4-(imidazolidin-2-on-1-ylmethyl)benzyloxy]-5-fluorophenyl}-4-methoxytetrahydropyran, and 4-{3-[3-((N',N'-dimethylaminocarbonyl)-N-methylamino)benzyloxy]-5-fluorophenyl}-4-methoxytetrahydropyran or a pharmaceutically acceptable salt thereof.

15. A pharmaceutically composition comprising a therapeutically effective amount of a compound as defined by claim 1 in combination with a pharmaceutically acceptable carrier.

16. A method of inhibiting 5-lipoxygenase enzyme activity in a mammal in need of such treatment comprising administering an effective amount of a compound as defined in claim 1.

* * * * *